US00PP17188P3

(12) United States Plant Patent
Jensen

(10) Patent No.: US PP17,188 P3
(45) Date of Patent: Nov. 7, 2006

(54) ***CAMPANULA* PLANT NAMED 'PKMP05'**

(50) Latin Name: *Campanula portenschlagiana*
Varietal Denomination: PKMP05

(75) Inventor: Gert Kim Jensen, Odense (DK)

(73) Assignee: Gartneriet PKM ApS, Odense (DK)

( * ) Notice: Subject to any disclaimer, the term of this patent is extended or adjusted under 35 U.S.C. 154(b) by 0 days.

(21) Appl. No.: 11/059,411

(22) Filed: Feb. 17, 2005

(65) Prior Publication Data

US 2006/0185046 P1 Aug. 17, 2006

(51) Int. Cl.
*A01H 5/00* (2006.01)

(52) U.S. Cl. ..... Plt./263
(58) Field of Classification Search ..... Plt./263
See application file for complete search history.

(56) References Cited

PUBLICATIONS

European Union Community Plant Variety Office (CPVO) 2004/2054 filed Nov. 3, 2004—documents include Feb. 28, 2006 print–out from CPVO website verifying application information (1 pg) and Proposal for Variety Denomination (1 pg), Application Papers (7 pgs) and Technical Questionnaire (5 pgs).

Canadian Plant Breeder's Rights 04/4488 filed Nov. 24, 2004—documents include Feb. 28, 2006 print–out from Canadian Food Inspection Agency—Plant Breeders' Rights Office List of Varieties verifying application information (1 pg) and Filing Receipt dated Nov. 26, 2004 (1 pg).

Japanese Plant Variety Rights 17737 filed Dec. 9, 2004—documents include Filing Receipt (w/English Translation) verifying application information (2 pgs) and Plant Variety Rights Application Papers (10 pgs).

*Primary Examiner*—Anne Marie Grunberg
*Assistant Examiner*—Georgia Helmer
(74) *Attorney, Agent, or Firm*—Foley & Lardner LLP

(57) ABSTRACT

A new and distinct cultivar of *Campanula* plant named 'PKMP05', characterized by having compact, upright plant habit; dense and bushy plant form mainly due to more upright stems; vigorous growth habit and no need for chemical growth retardation; greater number of flowers per plant, large upright violet flowers, and no need for vernalization.

3 Drawing Sheets

Botanical designation: *Campanula portenschlagiana.*
Variety denomination: 'PKMP05'.

BACKGROUND OF THE INVENTION

The present invention relates to a new and distinct cultivar of *Campanula* plant, botanically known as *Campanula portenschlagiana* Schult., commonly known as Dalmatian Bellflower, and hereinafter referred to by the name 'PKMP05'.

The new *Campanula,* 'PKMP05', is a product of a planned breeding program conducted by the inventor, Gert K. Jensen, in Søhus, Denmark. The objective of the breeding program is to develop a new *Campanula* variety with uniform and compact plant form and deep purple flowers.

The new *Campanula* cultivar originated from a cross made in 2002 by the inventor between a proprietary selection of *Campanula portenschlagiana* Schult named 'PKMP01', as the female parent and described in allowed U.S. patent application Ser. No. 10/648,304, and a proprietary selection of *Campanula portenschlagiana* Schult named '08.98.05' as the male parent (unpatented). The inventor selected the new *Campanula* cultivar from the progeny of the above cross in 2002 on the basis of its compact and freely flowering habit. Plants of the new *Campanula* are more upright, compact and more freely flowering than plants of both parental selections.

Asexual reproduction of the new *Campanula* cultivar by terminal cuttings taken and propagated since January of 2002 in Søhus, Denmark, has shown that the combination of characteristics as herein disclosed for the new cultivar are firmly fixed and retained through successive generations of asexual reproduction. The new cultivar reproduces true-to-type.

SUMMARY OF THE INVENTION

The following traits have been repeatedly observed and are determined to be the unique characteristics of 'PKMP05'. These characteristics in combination distinguish 'PKMP05' as a new and distinct cultivar:

1. Upright plant habit;
2. Dense and bushy plant form, mainly due to more upright stems;
3. Vigorous growth habit, and less need for chemical growth retardation;
4. More uniform and deeper purple flower color; and
5. No need for vernalization.

Side-by-side comparisons between the instant plant and the parental cultivars, 'PKMP01' and '08.98.05', were conducted by the inventor in Stige, Denmark. Plants of 'PKMP05' differ from the cultivars 'PKMP01' and '08.98.05' in the following characteristics:

1. Plants of 'PKMP05' have longer internodes than plants of the cultivars 'PKMP01' and '08.98.05'.
2. Plants of 'PKMP05' have darker gray-green colored leaves whereas plants of the cultivars 'PKMP01' and '08.98.05' have green-colored leaves.
3. Plants of 'PKMP05' have longer flower peduncles than plants of the cultivars 'PKMP01' and '08.98.05'.
4. Plants of 'PKMP05' are shorter and more compact than plants of the cultivars 'PKMP05' and '08.98.05'.

Of the many commercial cultivars known to the inventor, the most similar in comparison to 'PKMP05' are the *Campanula portenschlagiana* Schult. parental cultivars 'PKMP01' and '08.98.05'.

BRIEF DESCRIPTION OF THE DRAWINGS

The accompanying colored photographs illustrate the overall appearance of the new cultivar 'PKMP05', showing the colors as true as it is reasonably possible to obtain in colored reproductions of this type. Colors in the photographs may differ slightly from the color values cited in the detailed botanical description, which more accurately describe the actual colors of 'PKMP05'.

DETAILED BOTANICAL DESCRIPTION

Figure 1:
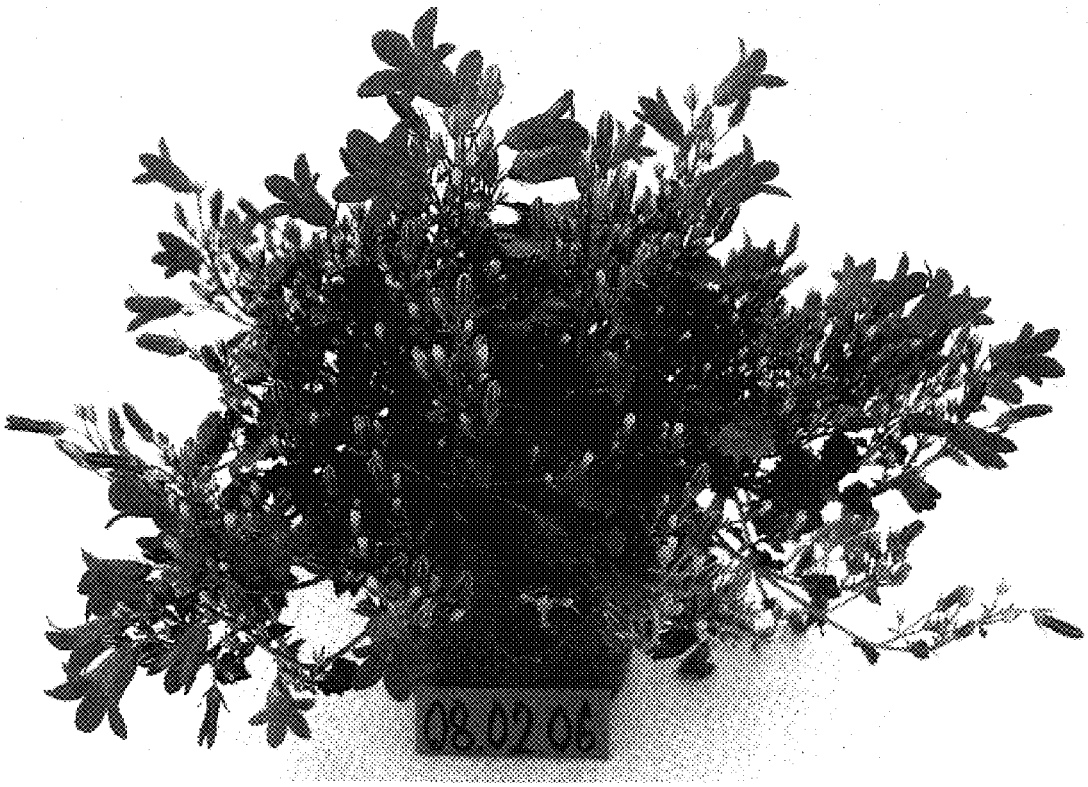
FIG. 1 shows a side perspective view of a typical flowering plant of 'PKMP05' (designated in the photograph by the breeder's reference, 08.02.06) as grown in a 10.5 cm pot.
Figure 2:
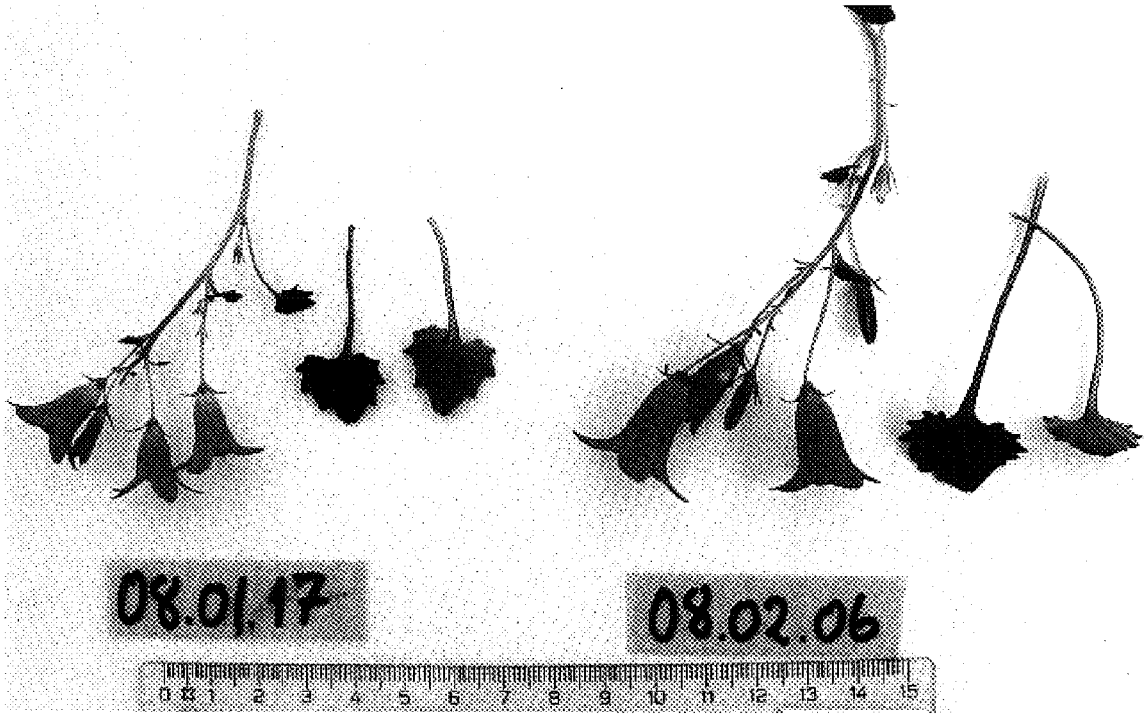
FIG. 2 shows a view of a typical flowering raceme and leaves of 'PKMP05' (designated in the photograph by the breeder's reference, 08.02.06) compared to a typical flowering raceme and leaves of the female parental cultivar, 'PKMP01' (designated in the photograph by the breeder's reference 08.01.17).
Figure 3:
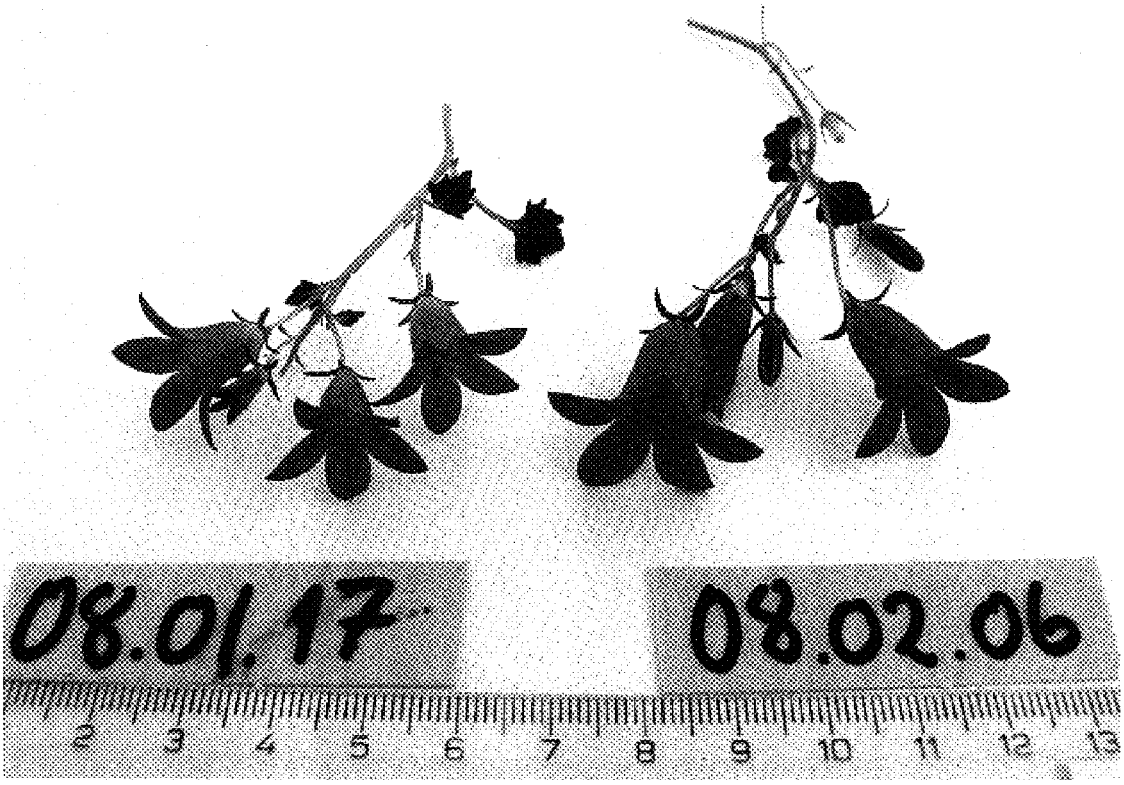
FIG. 3 shows a close-up view of a typical flowering raceme of 'PKMP05' (designated in the photograph by the breeder's reference, 08.02.06) compared to a close-up view of a typical flowering raceme of the female parental cultivar, 'PKMP01' (designated in the photograph by the breeder's reference 08.01.17).

The new *Campanula* cultivar 'PKMP05' has not been observed under all possible environmental conditions. The phenotype of the new cultivar may vary significantly with variations in environment such as temperature, light intensity, day length, and fertility level without any variance in genotype.

The aforementioned photographs, together with the following observations, measurements and values describe plants of the new *Campanula* cultivar 'PKMP05' as grown in a heated and lighted, glass-covered greenhouse in Søhus, Denmark, under conditions which closely approximate those generally used in commercial practice. Plants of 'PKMP05' are grown in a glass-covered greenhouse where day temperatures in the greenhouse range from 18–22° C. and the average night temperatures is 16° C. Light levels used while growing plants of 'PKMP05' are 55 $Wm^2$. Plants of 'PKMP05' are grown with 16 to 18 hour long day photoperiodic treatments; 10 hour short day photoperiodic treatments for propagation and seedlings.

The age of the 'PKMP05' plants described is 14 weeks old after cutting, as grown in 10.5 cm pots. The photographs and descriptions were taken during the winter season when day temperature in the glass-covered greenhouse ranged from 18–22° C. and when the night average temperatures in the glass-covered greenhouse was 16° C.

Color references are made to The Royal Horticultural Society Colour Chart (R.H.S.), $4^{th}$ ed., except where general colors of ordinary significance are used.

Classification:

*Botanical.*—*Campanula portenschlagiana.*

Parentage:

*Female parent.*—Proprietary selection of *Campanula portenschlagiana* Schult named 'PKMP01' (described in allowed U.S. patent application Ser. No. 10/648,304).

*Male parent.*—Proprietary selection of *Campanula portenschlagiana* Schult named '08.98.05' (unpatented).

Propagation:

*Type cutting.*—Terminal vegetative cuttings.

*Time to initiate roots.*—About 10 to 14 days at 18 to 21° C. in tunnels in a greenhouse.

*Root description.*—Fine, well branched.

Plant description:

*Form.*—Perennial, rosette plant with upright plant habit. Campanulate flowers in racemes. Freely branching with lateral branches forming at every node; dense and bushy.

*Crop time.*—After rooting, about 14 weeks are required to produce finished flowering plants in 10.5 cm pots.

*Plant height* (*soil level to top of plant plane*).—About 13 cm.

*Plant spread* (*width*).—About 27 cm.

*Lateral branches.*—Quantity: About 85–90 per plant. Length (including flowers): 10 cm. Branch diameter: 1–2 mm. 5 leaves per lateral branch.

*Internode length.*—25 mm.

*Stem.*—RHS 141B, green, in color.

*Vigor.*—Vigorous growth rate.

*Foliage description.*—Leaves single, dentate, cordate, palmate venation. Length: 15–20 mm. Width: About 25 mm. Shape: Cordate. Apex: Rounded. Base: Cordate. Margin: Broadly dentate. Texture: Smooth, glabrous, dull. Color: Upper surfaces (young and mature foliage) RHS N138A, green; Lower surfaces (young and Mature foliage): RHS 138A, green.

*Venation.*—Color: (upper and lower surfaces) RHS N138A, green. Pattern: palmate.

*Petiole.*—Length: 4–5 cm. Diameter: 1–2 mm. Texture: Smooth, glabrous. Color: RHS N138B, green.

Flower description:

*Flower number per plant.*—About 1500.

*Flower arrangement and shape.*—Single, upright, flowers in racemes; campanulate flowers with small star shaped calyx.

*Natural flowering season.*—Continuous throughout the spring and summer. Season can be extended by long day treatments, no vernalization needed.

*Flower longevity on the plant.*—About 5–9 days; however, longevity of individual flowers is highly dependent on temperature and light conditions. Flowers persistent.

*Fragrance.*—None.

*Number of flowers per inflorescence.*—9.

*Inflorescence size.*—Length: About 8 cm. Diameter: About 23 cm.

*Flowers.*—Length: about 18 mm. Diameter: about 23 mm. Lanceolate, acuminate petal lobes: 7 mm long and 5 mm wide. Corolla color: upper and lower surfaces, RHS N87A, violet, and RHS N88D, violet, and the bottom of the bell has this same violet color.

*Buds.*—Length: up to 15 mm. Diameter: up to 4 mm. Shape: oblong, ridged. Color: RHS 143C, green to RHS 84A–84D, violet, on the edges.

*Petals.*—Arrangement: Single, sympetalous, campanulate. Quantity per flower: 5. Length: 8–10 mm. Width: 7 mm. Overall shape: Arrow-shaped. Apex: Acute. Base: Fused. Margin: Entire. Texture: Velvety. Color (when opening): upper surface RHS 87A, violet, and lower surface RHS N82D, purple-violet. Color (when opened): upper surface RHS N87A, violet, and lower surface RHS N88D, violet. No fading, but withers to RHS 156C, gray-white.

*Sepals.*—Arrangement: Shiny, glabrous, free. Quantity per flower: 5. Length: 3 mm. Width: 1 mm. Overall shape: Arrow-shaped. Apex: Cuspidate. Base: Fused. Margin: Entire. Color: (immature — both surfaces) RHS 144B, yellow-green. Color: (mature — both surfaces) RHS 138A, green.

*Peduncles.*—Strength: Moderately strong. Length: About 30 mm. Diameter: About 1 mm. Color: 141B, green.

Reproductive organs:

*Androecium.*—Stamen: Quantity: 5; fused until pollen has been shed. Anther: Shape: Fused, after shedding curling. Length: About 1 mm. Color: RHS 158B, yellow-white. Pollen: Amount: Average production. Color: RHS 158B, yellow-white.

*Gynoecium.*—Pistil: Quantity: 1. Length: About 12 mm. Stigma: Shape: Tripartite. Color: RHS 85A, violet. Style: Length: About 11 mm. Color: RHS 84B, violet. Ovary: Color: RHS 150D, yellow-green.

*Seeds.*—Quantity: 25 per flower. Length: About 1 mm. Diameter: About 0.3 mm. Texture: Smooth and glabrous. Color: Greyed-orange, RHS 175A.

*Fruit.*—Type: Capsule. Length: About 6 to 8 mm. Diameter: About 2–3 mm. Color: RHS 164C, greyed-orange.

*Growth retardants.*—No growth retardants were used in the breeding program.

*Weather tolerance.*—Plants of the new *Campanula* have exhibited good tolerance to drought, rain and wind, with low temperature resistance to −20° C.

Disease/pest resistance: 'PKMP05' is not resistant to any diseases or pests typical to *Campanula* cultivars.

Disease/pest susceptibility: 'PKMP05' is susceptible to *Botrytis.*

I claim:

1. A new and distinct cultivar of *Campanula* plant named 'PKMP05', as illustrated and described herein.

* * * * *